United States Patent
Kawazoe

(10) Patent No.: US 7,342,138 B2
(45) Date of Patent: Mar. 11, 2008

(54) PROCESS FOR PRODUCING AROMATIC ALDEHYDE

(75) Inventor: Kentaro Kawazoe, Shizuoka (JP)

(73) Assignee: Ihara Chemical Industry Co., Ltd., Tokyo (JP)

( * ) Notice: Subject to any disclaimer, the term of this patent is extended or adjusted under 35 U.S.C. 154(b) by 15 days.

(21) Appl. No.: 10/569,469

(22) PCT Filed: Aug. 27, 2003

(86) PCT No.: PCT/JP03/10872

§ 371 (c)(1),
(2), (4) Date: Feb. 24, 2006

(87) PCT Pub. No.: WO2005/023745

PCT Pub. Date: Mar. 17, 2005

(65) Prior Publication Data

US 2007/0004934 A1    Jan. 4, 2007

(51) Int. Cl.
C07C 45/29    (2006.01)
C07C 45/37    (2006.01)

(52) U.S. Cl. .................................... 568/426; 568/437
(58) Field of Classification Search ................ None
See application file for complete search history.

(56) References Cited

FOREIGN PATENT DOCUMENTS

| JP | 1-050836 A | 2/1989 |
|---|---|---|
| JP | 01-151534 A | 6/1989 |
| JP | 9-077705 A | 3/1997 |
| JP | 09-087227 A | 3/1997 |

OTHER PUBLICATIONS

"Oxidation of Alcohols and Ethers Using Sodium Bromate-Hydrobromic Acid System", Kajigaeshi et al, *Bulletin of the Chemical Society of Japan*, 1986 vol. 59, No. 3, pp. 747-750.
Habib Firouzabadi et al., "Efficient Oxidation of Organic Compounds with Sodium and Silver Bromates NaBrO₃, AgBr O₃, in Non-Aqueous Solvents in the Presence of Lewis Acids", Bulletin of the Chemical Society of Japan, vol. 68, No. 8, pp. 2319-2325, XP008066058.
Ahmad Shaabani et al., "NaBrO₃-FeCl₃ as a new reagent for oxidation of benzylic and secondary alcohols to carbonyl compounds", Indian Journal of Chemistry, Section B: Organic Chemistry Including Medicinal Chemistry, vol. 40B (2), pp. 148-151, XP008066042.
Ahmad Shaabani et al., "Oxidation Deprotection of Trimethylsilyl Ethers to Carbonyl Compounds by NaBrO₃-NH₄Cl Reagent in Aqueous Acetonitrile", Synthetic Communications, vol. 31, No. 5, pp. 759-765, 2001.

*Primary Examiner*—Sikarl A. Witherspoon
(74) *Attorney, Agent, or Firm*—Arent Fox LLP

(57) ABSTRACT

A process for producing an aromatic aldehyde compound represented by a general formula (3):

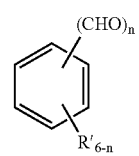

(3)

(wherein R' and n are as defined below), which comprises reacting a benzyl compound represented by a general formula (1):

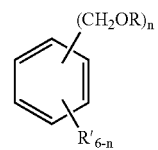

(1)

(wherein R may represents hydrogen atom, n represents an integer of 1 to 6, and R' may be the same or different and represent a hydrogen atom or an alkyl gorup, an alkyl group or a phenyl group which may have a substituent) with an oxy-compound of bromine represented by the formula (2):

$$MBrO_m \quad (2)$$

(wherein M represents a hydrogen atom or a metal atom, and m represents an integer of 1 to 3) in the presence of an acid catalyst. According to this method, an aromatic aldehyde compound can be produced in high selectivity by a simple operation without using an expensive catalyst or transition metal.

5 Claims, No Drawings

PROCESS FOR PRODUCING AROMATIC ALDEHYDE

CROSS-REFERENCE TO RELATED APPLICATION

This application is a National Stage entry of International Application No. PCT/JP03/10872, filed Aug. 27, 2003. The disclosure of the prior application is hereby incorporated herein in its entirety by reference.

TECHNICAL FIELD

The present invention relates to a process for producing a corresponding aromatic aldehyde compound by oxidizing a benzyl alcohol compound or a benzyl ether compound.

BACKGROUND ART

As a process for producing a corresponding aromatic aldehyde compound by oxidizing a benzyl alcohol compound, there have hitherto been known various methods for oxidation reaction, inclusive of: e.g., oxidation with chromic acid, oxidation with active manganese dioxide, oxidation with dimethyl sulfoxide typified by Swern oxidation, oxidation with an oxoammonium salt compound such as 2,2,6,6-tetramethylpiperidinooxy free radical (TEMPO), and oxidation with a transition metal catalyst such as ruthenium catalyst [JIKKEN KAGAKU KOZA (Experimental Chemistry Course), edited by The Chemical Society of Japan, Organic Synthesis III-Aldehyde•Ketone•Quinone-, 4th edition, MARUZEN Co., Ltd., 1991, Vol. 21, pp. 1-20].

However, in the method for oxidation with chromic acid or active manganese dioxide among the above-mentioned conventional methods, the residual harmful metal compound must be treated after the completion of the reaction. In the method for oxidation with dimethyl sulfoxide, an equivalent or more of an activating agent such as dicyclohexylcarbodiimide (DCC) or acid chloride must be used. Furthermore, in the method for oxidation with an oxoammonium salt compound and the method for oxidation with a transition metal catalyst, an expensive catalyst must be used.

Also, there has been known oxidation with hydrogen peroxide water in the presence of a catalytic amount of sodium tungstate [Tetrahedron Lett., Vo. 39, pp. 7549 (1998)]. However, a problem such as poor reactivity has still been unsolved, with respect to a compound having a substituent such as nitro group.

Furthermore, there has been known a method in which one equivalent of sodium bromate is used in an acetonitrile-water solvent mixture in the presence of 1.5 equivalents of ammonium chloride [J. Chem. Research(s), pp. 100 (1998)]. However, the use of a stoichiometric three-fold amount of an oxidizing agent and a treatment of one equivalent of sodium bromide as a waste are not preferable from industrial point of view.

DISCLOSURE OF THE INVENTION

An object of the present invention is to provide a novel process for producing an aromatic aldehyde compound in which the above-mentioned problem encountered in the prior art has been solved.

Another object of the present invention is to provide a novel process for producing a corresponding aromatic aldehyde compound by oxidizing a benzyl alcohol compound or a benzyl ether compound.

As a result of earnest study, the present inventor has surprisingly found that it is remarkably effective in solving the above-mentioned problem to react a benzyl alcohol compound or a benzyl ether compound with a small amount approximately corresponding to the stoichiometric amount (a small amount less than the stoichiometric amount, in some cases) of oxy-compound of bromine. The present invention has been completed based on such a discovery.

BEST MODES FOR CARRYING OUT THE INVENTION

The present invention will now be described in detail with reference to the accompanying drawing, as desired. In the following description, parts and percentages, which indicate a quantitative ratio, are by weight unless otherwise specifically noted.

The present invention includes, e.g., the following embodiments [1] to [11].

[1] A process for producing an aromatic aldehyde compound represented by a general formula (3):

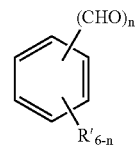

(wherein R' and n are as defined below), comprising: reacting a benzyl compound represented by a general formula (1):

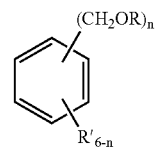

(wherein R represents a hydrogen atom or an alkyl group, n represents an integer of 1 to 6, and R' may be the same or different and each independently represents a hydrogen atom, an alkyl group, a hydroxyl group, an alkoxy group, a hydroxyalkyl group, an alkoxyalkyl group, a haloalkyl group, a carboxyl group or a metal salt thereof, an alkoxycarbonyl group, a halogen atom, a nitro group, an amino group, an alkylamino group, an alkylcarbonylamino group, a cyano group, a formyl group, an alkylcarbonyl group, or a phenyl group which may have a substituent), with an oxy-compound of bromine represented by a general formula (2):

(wherein M represents a hydrogen atom or a metal atom, and m represents an integer of 1 to 3) in the presence of an acid catalyst.

[2] A process for producing an aromatic aldehyde compound according to [1], wherein, in the benzyl compound represented by a general formula (1), all R'(s) are hydrogen atoms or at least one of R'(s) is an electron-withdrawing group.

[3] A process for producing an aromatic aldehyde compound according to [1], wherein, in the benzyl compound represented by a general formula (1), all R'(s) are hydrogen atoms or at least one of R'(s) is at least one of a nitro group, a chloro group and a hydroxymethyl group.

[4] A process for producing an aromatic aldehyde compound according to any one of claims 1 to 3, wherein the oxy-compound of bromine represented by a general formula (2) is bromic acid, bromate or bromite.

[5] A process for producing an aromatic aldehyde compound according to any one of [1] to [3], wherein the oxy-compound of bromine represented by a general formula (2) is bromate.

[6] A process for producing an aromatic aldehyde compound according to any one of [1] to [3], wherein the acid catalyst is an organic carboxylic acid.

[7] A process for producing an aromatic aldehyde compound according to any one of [1] to [3], wherein the acid catalyst is acetic acid.

[8] A process for producing an aromatic aldehyde compound according to any one of [1] to [3], wherein the oxy-compound of bromine represented by a general formula (2) is bromate or bromite and the acid catalyst is an organic carboxylic acid.

[9] A process for producing an aromatic aldehyde compound according to any one of [1] to [3], wherein the oxy-compound of bromine represented by a general formula (2) is bromate and the acid catalyst is an organic carboxylic acid.

[10] A process for producing an aromatic aldehyde compound according to any one of [1] to [3], wherein the oxy-compound of bromine represented by a general formula (2) is bromate or bromite and the acid catalyst is acetic acid.

[11] A process for producing an aromatic aldehyde compound according to any one of [1] to [3], wherein the oxy-compound of bromine represented by a general formula (2) is bromate and the acid catalyst is acetic acid.

(Process for Producing Aromatic Aldehyde Compound)

The process according to the present invention is a process for producing an aromatic aldehyde compound represented by a general formula (3) by reacting a benzyl compound represented by a general formula (1) with a oxy-compound of bromine represented by a general formula (2) in the presence of an acid catalyst.

(Benzyl Compound)

First, the benzyl compound represented by a general formula (1) (hereinafter, sometimes referred to as "raw material benzyl compound") used as a raw material for the process according to the present invention will be described.

R in a general formula (1) represents a hydrogen atom; or a linear or branched $C_1$-$C_6$ alkyl group such as methyl group, ethyl group, n-propyl group, isopropyl group, n-butyl group, sec-butyl group, t-butyl group, n-pentyl group, or n-hexyl group. In view of reactivity, R may preferably be a hydrogen atom or an alkyl group having 1 to 3 carbon atoms.

R' in a general formula (1) may be the same or different and each independently represents a hydrogen atom; a linear or branched $C_1$-$C_6$ alkyl group having 1 to 6 carbon atoms (hereinafter, when a group has 1 to 6 carbon atoms, the group is abbreviated to a "$C_1$-$C_6$ group") such as methyl group, ethyl group, n-propyl group, isopropyl group, n-butyl group, sec-butyl group, t-butyl group, n-pentyl group, or an n-hexyl group; a hydroxyl group; a linear or branched $C_1$-$C_6$ alkoxy group such as methoxy group, ethoxy group, n-propoxy group, or isopropoxy group; a linear or branched $C_1$-$C_6$ hydroxyalkyl group such as hydroxymethyl group or hydroxyethyl group; a linear or branched ($C_1$-$C_6$ alkoxy)-($C_1$-$C_6$ alkyl) group such as methoxymethyl group, methoxyethyl group, meth- oxyethyl group, or ethoxyethyl group; a linear or branched $C_1$-$C_6$ haloalkyl group such as fluoromethyl group, difluoromethyl group, or trifluoromethyl group; a carboxyl group or a metal salt thereof; a linear or branched ($C_1$-$C_6$ alkoxy) carbonyl group such as methoxycarbonyl group or ethoxycarbonyl group; a halogen atom such as bromine, chlorine, fluorine, or iodoine atom; nitro group; an amino group; a linear or branched mono or di($C_1$-$C_6$ alkyl)amino group such as methylamino group, dimethylamino group, ethylamino group, or diethylamino group; a linear or branched ($C_1$-$C_6$ alkyl)carbonylamino group such as acetylamino group, propionylamino group, or butyrylamino group; a cyano group; a formyl group; a linear or branched ($C_1$-$C_6$ alkyl)carbonyl group such as methylcarbonyl group or ethylcarbonyl group; or a phenyl group (the phenyl group may have a substituent, for example, a linear or branched $C_1$-$C_6$ alkyl group such as methyl group, ethyl group, n-propyl group, isopropyl group, n-butyl group, sec-butyl group, t-butyl group, n-pentyl group, or n-hexyl group; a hydroxyl group; a linear or branched $C_1$-$C_6$ alkoxy group such as methoxy group, ethoxy group, n-propoxy group, or isopropoxy group; a linear or branched $C_1$-$C_6$ hydroxyalkyl group such as hydroxymethyl group or hydroxyethyl group; a linear or branched ($C_1$-$C_6$ alkoxy)-($C_1$-$C_6$ alkyl) group such as methoxymethyl group, methoxyethyl group, or ethoxyethyl group; a linear or branched $C_1$-$C_6$ haloalkyl group such as fluoromethyl group, difluoromethyl group, or trifluoromethyl group; a carboxyl group or a metal salt thereof; a linear or branched ($C_1$-$C_6$ alkoxy)carbonyl group such as methoxycarbonyl group or ethoxycarbonyl group; a halogen atom such as bromine, chlorine, fluorine or iodine atom; a nitro group; an amino group; a linear or branched mono or di($C_1$-$C_6$ alkyl)amino group such as methylamino group, dimethylamino group, ethylamino group, or diethylamino group; a linear or branched $C_1$-$C_6$ alkylcarbonylamino group such as acetylamino group, propionylamino group, or butyrylamino group; a cyano group; a formyl group; or a linear or branched ($C_1$-$C_6$ alkyl)carbonyl group such as methylcarbonyl group or ethylcarbonyl group).

In view of reactivity, R' may preferably be a hydrogen atom; or an electron-withdrawing group such as $C_1$-$C_6$ hydroxyalkyl group, ($C_1$-$C_6$ alkoxy)-($C_1$-$C_6$ alkyl) group, $C_1$-$C_6$ haloalkyl group, carboxyl group or a metal salt thereof, ($C_1$-$C_6$ alkoxy)carbonyl group, halogen atom, nitro group, ($C_1$-$C_6$ alkyl)carbonylamino group, cyano group, formyl group, or ($C_1$-$C_6$ alkyl)carbonyl group.

Among these substituents, R' may preferably be a hydrogen atom, a $C_1$-$C_6$ hydroxyalkyl group, a $C_1$-$C_6$ haloalkyl group, a carboxyl group or a metal salt thereof, a ($C_1$-$C_6$ alkoxy)carbonyl group, a halogen atom, a nitro group, a cyano group, a formyl group, or a ($C_1$-$C_6$ alkyl)carbonyl group, and may be particularly preferably a hydrogen atom, a nitro group, a halogen atom, or a $C_1$-$C_6$ hydroxyalkyl group. Furthermore, good results may be obtained when R' is a hydrogen atom, a nitro group, a chloro group, or a hydroxymethyl group.

n in a general formula (1) represents an integer of 1 to 6. In the process according to the present invention, n may preferably be from 1 to 3 in view of availability of a raw material and reactivity.

(Specific Examples of Benzyl Compound)

Specific examples of the benzyl compound represented by a general formula (1) (raw material benzyl compound), which can be used in this reaction, include benzyl alcohol, methoxymethylbenzene, o-hydroxymethyltoluene, m-hydroxymethyltoluene, p-hydroxymethyltoluene, o-methoxymethyltoluene, m-methoxymethyltoluene, p-methoxymethyltoluene, o-hydroxymethyl phenol, m-hydroxymethyl phenol, p-hydroxymethyl phenol, o-methoxymethyl phenol, m-methoxymethyl phenol, p-methoxymethyl phenol, o-methoxybenzyl alcohol, m-methoxybenzyl alcohol, p-methoxybenzyl alcohol, o-methoxymethoxymethylbenzene, m-methoxymethoxymethylbenzene, p-methoxymethoxymethylbenzene, o-xylylene glycol, m-xylylene glycol, p-xylylene glycol, o-xylylene glycol monomethyl ether, m-xylylene glycol monomethyl ether, p-xylylene glycol monomethyl ether, o-xylylene glycol dimethyl ether, m-xylylene glycol dimethyl ether, p-xylylene glycol dimethyl ether, o-fluoromethylbenzyl alcohol, m-fluoromethylbenzyl alcohol, p-fluoromethyl-benzyl alcohol, o-methoxymethyl-fluoromethylbenzene, m-methoxymethyl-fluoromethylbenzene, p-methoxymethyl-fluoromethylbenzene, o-hydroxymethylbenzoic acid, m-hydroxymethylbenzoic acid, p-hydroxymethylbenzoic acid, o-methoxymethylbenzoic acid, m-methoxymethylbenzoic acid, p-methoxymethylbenzoic acid, methyl o-hydroxymethylbenzoate, methyl m-hydroxymethylbenzoate, methyl p-hydroxymethylbenzoate, methyl o-methoxymethylbenzoate, methyl m-methoxymethylbenzoate, methyl p-methoxymethylbenzoate, o-chlorobenzyl alcohol, m-chlorobenzyl alcohol, p-chlorobenzyl alcohol, o-chlorobenzyl methyl ether, m-chlorobenzyl methyl ether, p-chlorobenzyl methyl ether, o-nitrobenzyl alcohol, m-nitrobenzyl alcohol, p-nitrobenzyl alcohol, o-nitrobenzyl methyl ether, m-nitrobenzyl methyl ether, p-nitrobenzyl methyl ether, o-hydroxymethylaniline, m-hydroxymethylaniline, p-hydroxymethylaniline, o-methoxymethylaniline, m-methoxymethylaniline, p-methoxymethylaniline, N-methyl-o-hydroxymethylaniline, N-methyl-m-hydroxymethylaniline, N-methyl-p-hydroxymethylaniline, N-methyl-o-methoxymethylaniline, N-methyl-m-methoxymethylaniline, N-methyl-p-methoxymethylaniline, o-hydroxymethylacetoanilide, m-hydroxymethylacetoanilide, p-hydroxymethylacetoanilide, o-methoxymethylacetoanilide, m-methoxymethylacetoanilide, p-methoxymethylacetoanilide, o-cyanobenzyl alcohol, m-cyanobenzyl alcohol, p-cyanobenzyl alcohol, o-cyanobenzyl methyl ether, m-cyanobenzyl methyl ether, p-cyanobenzyl methyl ether, o-hydroxymethylbenzaldehyde, m-hydroxymethylbenzaldehyde, p-hydroxymethylbenzaldehyde, o-methoxymethylbenzaldehyde, m-methoxymethylbenzaldehyde, p-methoxymethylbenzaldehyde, o-hydroxymethylacetophenone, m-hydroxymethylacetophenone, p-hydroxymethylacetophenone, o-methoxymethylacetophenone, m-methoxymethylacetophenone, p-methoxymethylacetophenone, 2-hydroxymethylbiphenyl, 3-hydroxymethylbiphenyl, 4-hydroxymethylbiphenyl, 2-methoxymethylbiphenyl, 3-methoxymethylbiphenyl, 4-methoxymethylbiphenyl, 4,4'-dihydroxymethylbiphenyl, and 4,4'-dimethoxymethylbiphenyl.

Among these benzyl compounds, a benzyl compound such as benzyl alcohol, o-, m-, or p-nitrobenzyl alcohol, o-, m-, or p-nitrobenzyl methyl ether, o-, m-, or p-chlorobenzyl alcohol, o-, m-, or p-chlorobenzyl methyl ether, o-, m-, or p-xylene glycol, or o-, m-, or p-xylene glycol monomethyl ether may preferably be used.

(Process for Producing Benzyl Compound)

The benzyl compound represented by a general formula (1) (raw material benzyl compound) is a known compound, or can be produced by a known method (with respect to details of these reactions, see, for example, documents "Justus Liegibs Annalen der Chemie, Vol. 143, pp. 81, 1867" and "Journal of the American Chemical Society, Vo. 46, pp. 967, 1924". Examples of such a "known method" include a method of hydrolyzing a corresponding benzyl chloride compound as a raw material in water, or a method of reacting a corresponding benzyl chloride compound with a metal alkoxide such as sodium alkoxide in a suitable organic solvent.

(Oxy-Compound of Bromine)

Subsequently, oxy-compound of bromine represented by a general formula (2) will be described.

M in a general formula (2) represents a hydrogen atom; or a metal atom of alkali metal such as sodium, potassium or lithium, and alkali earth metal such as magnesium or calcium.

m in a general formula (2) represents an integer of 1 to 3.

Therefore, specific examples of the oxy-compound of bromine represented by a general formula (2), which can be used in this reaction, bromic acid; bromate typified by bromic acid metal salt such as sodium bromate, potassium bromate, or calcium bromate; bromous acid; bromite typified by bromous acid metal salt such as sodium bromite or potassium bromite; hypobromous acid; and hypobromite. These oxy-compounds of bromine can also be used in the form of a hydrate.

In view of availability, ease of handling and reactivity, bromic acid, bromate and bromite may preferably be used, and bromate may be particularly preferably used.

These oxy-compound of bromines represented by a general formula (2) are known compounds.

(Molar Ratio of Oxy-Compound of Bromine)

With respect to a molar ratio of the oxy-compound of bromine represented by a general formula (2) to be used in this reaction, as far as the reaction proceeds, a molar ratio of the oxy-compound of bromine to the benzyl compound represented by a general formula (1) (raw material benzyl compound) is not specifically limited. To suppress the side reaction, the molar ratio of oxy-compound of bromine represented by a general formula (2) may be usually within a range from 0.3 to 0.5 mols, and preferably from 0.33 to 0.4 mols, based on 1 mol of the benzyl compound represented by a general formula (1) (raw material benzyl compound) when m in a general formula (2) is 3. When m in a general formula (1) is 2, the molar ratio of the oxy-compound of bromine may be usually within a range from 0.45 to 0.75 mols, and preferably from 0.5 to 0.6 mols. When m in a general formula (1) is 1, the molar ratio of the oxy-compound of bromine may be usually within a range from 0.9 to 1.5 mols, and preferably from 1.0 to 1.2 mols.

When the benzyl compound represented by a general formula (1) (raw material benzyl compound) has a plurality of groups —$CH_2OR$ (hydroxymethyl group, alkoxymethyl group) (that is, a raw material benzyl compound is a compound of a general formula (1) wherein n is from 2 to 6, or a compound wherein R' is a phenyl group substituted with a group —$CH_2OR$, or a compound which may satisfy both requirements), and it is intended to convert all groups —$CH_2OR$ into formyl groups, it is necessary to use the oxy-compound of bromine in a molar ratio obtained by multiplying the molar ratio of the oxy-compound of bromine to be used by the total number of substituents.

When the raw material benzyl compound has a plurality of groups —$CH_2OR$, as described above, only a portion of a plurality of groups —$CH_2OR$ can be converted into formyl groups by controlling the molar ratio of the oxy-compound of bromine represented by a general formula (2).

(Acid Catalyst)

This reaction is conducted using an acid catalyst. Examples of the acid catalyst, which can be used in this reaction, include carboxylic acid such as acetic acid, propionic acid, trifluoroacetic acid, fluoroacetic acid, lactic acid, or amino acid; organic acid typified by organic sulfonic acid such as p-toluenesulfonic acid, methanesulfonic acid, or benzenesulfonic acid; inorganic acid such as hydrochloric acid, sulfuric acid, or phosphoric acid; Lewis acid such as aluminum chloride, boron trifluoride-tetrahydrofuran complex ($BF_3$-THF complex), or polyphosphoric acid; and solid acid. Among these acids, carboxylic acid such as acetic acid or propionic acid may preferably be used in view of availability and ease of handling.

The amount of the acid catalyst to be used in this reaction is not specifically limited as far as the reaction sufficiently proceeds, but may be within a range from 0.01 to 100 mols, and preferably from 0.05 to 10 mols, based on 1 mol of benzyl compound represented by a general formula (1) (raw material benzyl compound) in view of the reaction rate and economical efficiency. However, the amount is not limited within the above range and an excess amount of the acid catalyst can be used while serving as a solvent described hereinafter.

(Solvent)

This reaction can be sufficiently conducted with or without using a solvent. The solvent which can be used in the reaction is not specifically limited as far as it does not exert an adverse influence on the reaction, and examples thereof include carboxylic acid such as acetic acid or propionic acid; water; aromatic hydrocarbons such as toluene, xylene, and chlorobenzene; halogenated aliphatic hydrocarbons such as dichloromethane and chloroform; acetate esters such as methyl acetate, ethyl acetate, and butyl acetate; aprotic polar solvents such as dimethyl formamide, dimethyl acetamide, N-methylpyrrolidone, tetramethylurea, hexamethylphosphorictriamide (HMPA), and propylene carbonate; ether-based solvents such as diethyl ether, tetrahydrofuran, and dioxane; and aliphatic hydrocarbons such as pentane and n-hexane. In view of solubility of an oxidizing agent and reactivity, carboxylic acid such as acetic acid or propionic acid, or water may preferably be used. It may be particularly preferable to use carboxylic acid as the solvent because it also serves as the acid catalyst. The above-mentioned solvents can be used alone or used as a solvent mixture in any mixing ratio.

The amount of the solvent may be any amount which enables well stirring of the reaction system. In view of the reaction rate, the amount of the solvent may be usually within a range from 0.05 to 10 L (liter), and preferably from 0.5 to 2 L, based on 1 mol of the benzyl compound represented by a general formula (1) (raw material benzyl compound). When the solvent has too low polarity, solubility of the oxidizing agent decreases and thus the reaction does not proceed smoothly. Therefore, it is undesirable.

(Reaction Temperature)

The reaction temperature of this reaction may be within a range from 0° C. to a reflux temperature of the solvent to be used, and preferably from 20 to 100° C.

When this reaction is carried out under high temperature conditions, vigorous heat generation may occur with rapid progress of the reaction. From such a point of view, it may be advantageous to employ a technique in which the temperature is carefully set to a low temperature, a technique in which a benzyl compound is added dropwise to the reaction system, a technique in which an oxy-compound of bromine is added to the reaction by several portions, and a technique in which a solution prepared by dissolving an oxy-compound of bromine in a solvent used or an aqueous oxy-compound of bromine solution is added dropwise to the reaction system.

(Reaction Time)

The reaction time of this reaction is not specifically limited, but may preferably be within a range from 1 to 30 hours, so as to suppress the production of by-product.

In this reaction, bromide ions ($Br^-$) generated with the progress of the reaction may partially react with a oxy-compound of bromine to generate a small amount of bromine. This bromine may react with the intended aromatic aldehyde compound produced in the system thereby to cause side reaction which can cause oxidation of the corresponding carboxylic acid. From such a point of view, the reaction may preferably be conducted under mild reaction conditions so as to prevent the generation of bromine if possible.

(Aromatic Aldehyde Compound)

After the completion of the reaction, the intended aromatic aldehyde compound can be isolated form the reaction mixture by a conventional method. Examples of such a "conventional method" include a method of distilling the reaction mixture and optionally rectifying the mixture, or a method of filtrating an intended product in the form of solid and optionally recrystallizing the product.

According to this reaction, an aromatic aldehyde compound represented by a general formula (3) is produced in high selectivity without causing excess oxidation reaction in which the oxidation stage of the product proceeds to produce a carboxylic acid compound. The resulting aromatic aldehyde compound represented by a general formula (3) is a compound which is useful as an intermediate of a drug and a agricultural chemical.

In the present invention, if a GC area to a carboxylic acid compound produced as by-product is 1, the intended aromatic aldehyde can be obtained in a GC area ratio of at least 20 or more, usually 45 or more, preferably 90 or more, and particularly preferably 99 or more.

EXAMPLES

The process for producing a compound of the present invention will now be described in detail by way of examples, but the present invention is not limited to the following examples.

Example 1

(An Embodiment of the Invention Described in the Above Embodiment [1]): Production of Benzaldehyde Into a 50 ml three-necked flask equipped with a magnetic stirrer, a reflux condenser and a thermometer, 4.32 g (40 mmols) of benzyl alcohol, 2.0 g (13.5 mmols) of sodium bromate, 10 ml (174 mmols) of acetic acid and 10 ml of water were charged, and then the resultant mixture was stirred at room temperature for 24 hours. Along with the progress of the reaction, a small amount of bromine was produced and the temperature of the reaction solution was raised to 30° C. After the completion of the reaction, bromine completely disappeared.

With respect to the components in the reaction solution, an area ratio as determined by gas chromatography of benzaldehyde was 91.7% and that of benzyl alcohol was 5.1%. Using n-tridecane as an internal standard substance, quantitative analysis was conducted by gas chromatography (GC). As a result, yield of benzaldehyde as the intended product of this reaction was 87.6%.

<GC Conditions>

GC analytical conditions used in this example are as follows.

Apparatus: mfd. by Shimadzu Corporation (trade name: GC9-AM)

Column: mfd. by Chemicals Evaluation and Research Institute, Japan (trade name: G-100, 1.0 μm in coating layer thickness×1.2 mm in inner diameter×20 m in length)

Injection temperature: 280° C.

Carrier gas: Nitrogen gas (20 ml/min)

Detector: FID

Measuring and determination apparatus: mfd. by Shimadzu Corporation (trade name: Chromatopak CR-8A)

Oven temperature conditions: Oven initial temperature: 180° C.; heating at 10° C./min for 10 minutes; after reaching 280° C., maintaining at the same temperature Example 2

(An Embodiment of the Invention Described in the Above Embodiment [1]): Production of o-nitrobenzaldehyde In a 300 ml three-necked flask equipped with a mechanical stirrer, a reflux condenser and a thermometer, 61.2 g (400 mmols) of o-nitrobenzyl alcohol, 20 g (135 mmols) of sodium bromate, 100 ml (1.74 mols) of acetic acid and 50 ml of water were charged, and then the resultant mixture was stirred at 50° C. for 3 hours. Along with the progress of the reaction, a small amount of bromine was produced and the temperature of the reaction solution was raised to 68° C. After the stirring of the mixture at 90° C. for one hour, 10 g (68 mmols) of sodium bromate was added thretо, and then the mixture was stirred at 70° C. for one hour and further stirred at 90° C. for one hour.

With respect to the components in the reaction solution, the intended o-nitrobenzaldehyde was produced in an area ratio, as determined by gas chromatography in the same manner as in Example 1, of 82.2%. It was confirmed that the reaction smoothly proceeds by the process according to the present invention even in case of a raw material benzyl compound wherein R' is an electron-withdrawing group such as nitro group.

Example 3

(An Embodiment of the Invention Described in the Above Embodiment [1]): Production of m-methoxybenzaldehyde In a 15 ml test tube type reaction vessel equipped with a magnetic stirrer and a reflux condenser, 0.55 g (4 mmols) of m-methoxybenzyl alcohol, 0.18 g (1.2 mmols) of sodium bromate and 2 ml (34.8 mmols) of acetic acid were charged, and then the resultant mixture was stirred at 90° C. for 1.5 hours. Along with the progress of the reaction, a small amount of bromine was produced. After the completion of the reaction, bromine completely disappeared.

With respect to the components in the reaction solution, the intended m-methoxybenzaldehyde was produced in an area ratio, as determined by gas chromatography, of 35.2% and 11.7% of m-methoxybenzyl alcohol as a raw material was remained. It was confirmed that the reaction proceeds by the process according to the present invention even in case of a raw material benzyl compound wherein R' is an electron-donating group such as methoxy group.

Example 4

(An Embodiment of the Invention Described in the Above Embodiment [1]): Production of Benzaldehyde In the same manner as in Example 3, the operation was conducted, except that 0.43 g (4 mmols) of benzyl alcohol was used in place of m-methoxybenzyl alcohol and 0.39 g (2 mmols) of sodium bromite trihydrate was used in place of sodium bromate, and also the mixture was stirred at 50° C. for 4 hours. With respect to the components in the reaction solution, the intended benzaldehyde was produced in an area ratio, as determined by gas chromatography, of 93.5%.

Example 5

(An Embodiment of the Invention Described in the Above Embodiment [1]): Production of Benzaldehyde In the same manner as in Example 3, the operation was conducted, except that 0.43 g (4 mmols) of benzyl alcohol was used in place of m-methoxybenzyl alcohol and 2 ml (26.8 mmols) of propionic acid was used in place of acetic acid, and also the mixture was stirred at 80° C. for 2.5 hours. With respect to the components in the reaction solution, the intended benzaldehyde was produced in an area ratio, as determined by gas chromatography, of 90.0%.

Example 6

(An Embodiment of the Invention Described in the Above Embodiment [1]): Production of o-nitrobenzaldehyde In the same manner as in Example 3, the operation was conducted, except that 0.67 g (4 mmols) of o-nitrobenzyl methyl ether was used in place of m-methoxybenzyl alcohol and also 0.2 g (1.35 mmols) of sodium bromate was used. With respect to the components in the reaction solution, the intended o-nitrobenzaldehyde was produced in an area ratio, as determined by gas chromatography, of 53.6% and 38.6% of o-nitrobenzyl methyl ether as a raw material was remained.

Example 7

(An Embodiment of the Invention Described in the Above Embodiment [1]): Production of o-nitrobenzaldehyde In the same manner as in Example 3, the operation was conducted, except that 0.61 g (4 mmols) of o-nitrobenzyl alcohol was used in place of m-methoxybenzyl alcohol and 2 ml of water and one drop of 47% bromic acid were used in place of 2 ml of acetic acid. With respect to the components in the reaction solution, the intended o-nitrobenzaldehyde was produced in an area ratio, as determined by gas chromatography, of 75.2% and 24.2% of o-nitrobenzyl alcohol as a raw material was remained.

Example 8

(An Embodiment of the Invention Described in the Above Embodiment [1]): Production of Benzaldehyde In the same manner as in Example 3, the operation was conducted, except that 0.43 g (4 mmols) of benzyl alcohol was used in place of m-methoxybenzyl alcohol and 1 ml (17.4 mmols) of acetic acid was used in place of 2 ml of acetic acid, and also 2 ml of dimethyl formamide and 0.2 g (1.35 mmols) of sodium bromate were used. With respect to the components in the reaction solution, the intended benzaldehyde was produced in an area ratio, as determined by gas chromatography, of 92.6%.

Example 9

(An Embodiment of the Invention Described in the Above Embodiment [1]): Production of Benzaldehyde In the same manner as in Example 8, the operation was conducted, except that 2 ml of propylene carbonate was used in place of 2 ml of dimethyl formamide. With respect to the components in the reaction solution, the intended benzaldehyde was produced in an area ratio, as determined by gas chromatography, of 93.4%.

Example 10

(An Embodiment of the Invention Described in the Above Embodiment [1]): Production of p-chlorobenzaldehyde In the same manner as in Example 3, the operation was conducted, except that 0.63 g (4 mmols) of p-chlorobenzyl methyl ether was used in place of m-methoxybenzyl alcohol and also 0.2 g (1.35 mmols) of sodium bromate was used. With respect to the components in the reaction solution, the intended p-chlorobenzaldehyde was produced in an area ratio, as determined by gas chromatography, of 91.0%.

Example 11

(An Embodiment of the Invention Described in the Above Embodiment [1]): Production of 4,4'-bisformylbiphenyl In the same manner as in Example 3, the operation was conducted, except that 0.53 g (2 mmols) of bismethoxymethylbiphenyl was used in place of m-methoxybenzyl alcohol and also 0.2 g (1.35 mmols) of sodium bromate was used. With respect to the components in the reaction solution, 4,4'-bisformylbiphenyl was produced in an area ratio, as determined by gas chromatography, of 93.3% and 6.7% of bismethoxymethylbiphenyl as a raw material was remained.

Example 12

(An Embodiment of the Invention Described in the Above Embodiment [1]): Production of o-phthalaldehyde In the same manner as in Example 3, the operation was conducted, except that 0.39 g (2 mmols) of o-xylylene glycol diethyl ether was used in place of m-methoxybenzyl alcohol and also 0.2 g (1.35 mmols) of sodium bromate was used. With respect to the components in the reaction solution, the intended o-phthalaldehyde was produced in an area ratio, as determined by gas chromatography, of 32.0% and o-ethoxymethylbenzaldehyde as a product at the intermediate stage (compound in which only one among two ethoxymethyl groups in a molecule of the raw material was replaced by a formyl group) was produced in an area ratio of 30.1%.

Example 13

(An Embodiment of the Invention Described in the Above Embodiment [1]): Production of p-phthalaldehyde In the same manner as in Example 3, the operation was conducted, except that 0.55 g (4 mmols) of p-xylylene glycol was used in place of m-methoxybenzyl alcohol and 1 ml (17.4 mmols) of acetic acid was used in place of 2 ml of acetic acid, and also 1 ml of water and 0.4 g (2.7 mmols) of sodium bromate were used. With respect to the components in the reaction solution, the intended p-phthalaldehyde was produced in an area ratio, as determined by gas chromatography, of 56.0% and p-hydroxymethylbenzaldehyde as a product at the intermediate stage (compound in which only one among two hydroxymethyl groups in a molecule of the raw material was replaced by a formyl group) was produced in an area ratio of 28.6%.

Example 14

(An Embodiment of the Invention Described in the Above Embodiment [1]): Production of Benzaldehyde In the same manner as in Example 3, the operation was conducted, except that 0.43 g (4 mmols) of benzyl alcohol was used in place of m-methoxybenzyl alcohol and 0.23 g (1.35 mmols) of potassium bromate was used in place of sodium bromate. With respect to the components in the reaction solution, the intended benzaldehyde was produced in an area ratio, as determined by gas chromatography, of 90.0%.

Example 15

(An Embodiment of the Invention Described in the Above Embodiment [1]): Production of Benzaldehyde In a 50 ml three-necked flask equipped with a magnetic stirrer, a reflux condenser and a thermometer, 21.6 g (200 mmols) of benzyl alcohol, 10.0 g (67 mmols) of sodium bromate and 20 ml (348 mmols) of acetic acid were charged, and then the resultant mixture was stirred at 75° C. for 8 hours. With the processing of the reaction, a small amount of bromine was produced and the temperature of the reaction solution was raised to 80° C. After the completion of the reaction, bromine completely disappeared. The reaction solution was cooled to room temperature and 100 ml of water was added. Under cooling in an ice bath, an aqueous 24% sodium hydroxide solution was added by several portions so as not to raise the liquid temperature until the pH is adjusted to 11 or higher. The resulting product was extracted in turn with 100 ml of ether and 50 ml of ether, and then the ether phase was washed with saturated saline. The ether phase was dried over anhydrous sodium sulfate and the solvent was distilled off under reduced pressure to obtain 19.1 g of an oil. With respect to the components in the oil, the intended benzaldehyde was produced in an area ratio, as determined by gas chromatography, of 89.4%. This oil was purified by distillation under reduced pressure [112 to 115° C./13.33 KPa (100 mmHg)] to obtain 13.6 g of benzaldehyde. Isolation yield: 64%.

Example 16

(An Embodiment of the Invention Described in the Above Embodiment [1]): Production of p-chlorobenzaldehyde In a 100 ml four-necked flask equipped with a magnetic stirrer, a reflux condenser and a thermometer, 31.3 g (200 mmols) of p-chlorobenzyl methyl ether, 10.0 g (67 mmols) of sodium bromate and 40 ml (696 mmols) of acetic acid were charged, and then the resultant mixture was stirred at 75° C. for 8 hours. With the processing of the reaction, a small amount of bromine was produced and the temperature of the reaction solution was raised to 80° C. After the completion of the reaction, bromine completely disappeared. After recovering 28 m of acetic acid under reduced pressure, the resulting reaction solution was cooled to room temperature and 100 ml of water was added. An aqueous 24% sodium hydroxide solution was added by several portions so as not to raise the liquid temperature until the pH is adjusted to 11 or higher. The resulting product was extracted twice with 100 ml of ethyl acetate and the ethyl acetate phase was washed with saturated saline. The ethyl acetate phase was dried over anhydrous sodium sulfate and the solvent was distilled off under reduced pressure to obtain 29.0 g of a solid. With respect to the components in the solid, the intended p-chlorobenzaldehyde was produced in an area ratio, as determined by gas chromatography, of 89.2%.

Comparative Example 1

Production of Benzaldehyde

In the same manner as in Example 4, the operation was conducted, except that 0.43 g (4 mmols) of benzyl alcohol was used in place of m-methoxybenzyl alcohol and 2 ml of dimethyl formamide in place of 2 ml of acetic acid and 0.2 g (1.35 mmols) of sodium bromate were used. With respect to the components in the reaction solution, an area ratio as determined by gas chromatography of the intended benzaldehyde was 1.3% and that of a raw material benzyl alcohol was 98.7%.

Comparative Example 2

Production of Benzaldehyde

In the same manner as in Example 4, the operation was conducted, except that 0.43 g (4 mmols) of benzyl alcohol was used in place of m-methoxybenzyl alcohol and 1.8 ml of toluene and 0.2 ml (3.5 mmols) of acetic acid were used in place of 2 ml of acetic acid, and also 0.2 g (1.35 mmols) of sodium bromate was used. With respect to the components in the reaction solution, an area ratio as determined by gas chromatography of the intended benzaldehyde was 2.2% and that of a raw material benzyl alcohol was 96.5%.

Comparative Example 3

Production of Benzaldehyde

In the same manner as in Example 4, the operation was conducted, except that 0.43 g (4 mmols) of benzyl alcohol was used in place of m-methoxybenzyl alcohol and 2 ml of water in place of 2 ml of acetic acid and 0.2 g (1.35 mmols) of sodium bromate were used. With respect to the components in the reaction solution, an area ratio as determined by gas chromatography of the intended benzaldehyde was 1.4% and that of a raw material benzyl alcohol was 97.9%.

Comparative Example 4

Production of Benzaldehyde

In the same manner as in Example 4, the operation was conducted, except that 0.43 g (4 mmols) of benzyl alcohol was used in place of m-methoxybenzyl alcohol and 1 ml (17.4 mmols) of acetic acid was used in place of 2 ml of acetic acid, and also 1 ml of water and 0.14 g (1.35 mmols) of sodium chlorate was used in place of sodium bromate. With respect to the components in the reaction solution, an area ratio as determined by gas chromatography of the intended benzaldehyde was 1.6%, that of benzyl alcohol was 77.9% and that of benzyl acetate was 20.5%.

Comparative Example 5

Production of Benzaldehyde

[Method Described in J. Chem. Research(s), pp. 100 (1998)]

In a 15 ml test tube type reaction vessel equipped with a magnetic stirrer and a reflux condenser, 0.43 g (4 mmols) of benzyl alcohol, 0.6 g (4 mmols) of sodium bromate, 0.32 g (6 mmols) of ammonium chloride, 5.6 ml of acetonitrile and 2.4 ml of water were charged, and then the resultant mixture was stirred at 80° C. for one hour. After 20 minutes, bumping occurred and bromine was vigorously produced. After the completion of the reaction, bromine completely disappeared. With respect to the components in the reaction solution, an area ratio as determined by gas chromatography of the intended benzaldehyde was 12.2%, that of a raw material benzyl alcohol was 36.1%, and that of benzoic acid was 36.2%.

Example 17

Production of o-iodobenzaldehyde

In a 25 ml Kjeldahl flask equipped with a magnetic stirrer and a reflux condenser, 2.30 g (9.8 mmols) of o-iodobenzyl alcohol and 5 ml of (87 mmols) of acetic acid were charged and an aqueous solution prepared by dissolving 0.50 g (3.33 mmols) of sodium bromate in 3 ml of water was added dropwise over 2 hours under stirring. After the completion of dropwise addition, stirring was conducted at 75° C. for 3 hours. With respect to the components in the reaction solution, an area ratio as determined by gas chromatography of the intended o-iodobenzaldehyde was 99.9% or more. It was confirmed by GS-MS that a molecular ion peak is 232.

Example 18

Production of o-methylbenzaldehyde

In a 100 ml four-necked flask equipped with a magnetic stirrer, a reflux condenser and a thermometer, 12.2 g (100 mmols) of o-methylbenzyl alcohol and 20 ml of (333 mmols) of acetic acid were charged and heated to 80° C. An aqueous solution prepared by dissolving 5.0 g (33 mmols) of sodium bromate in 20 ml of water was added dropwise over one hours so as not to raise the temperature in the system to 90° C. or higher. After the stirring of the mixture for one hour, 0.2 g (1.35 mmols) of sodium bromate was further added, and then the mixture was stirred for one hour until a red color of bromine disappears. An aqueous sodium carbonate solution was added to the system until the system is alkalified, followed by extraction twice with 100 ml of ether. The ether phase was washed with saturated saline and the solvent was distilled off under reduced pressure to obtain 12.5 g of an oil. The resulting oil was purified by silica gel column chromatography (ethyl acetate:n-hexane=1:4) to obtain 11.8 g of o-methylbenzaldehyde. Yield: 98.3%. It was confirmed by GS-MS that a molecular ion peak is 120.

Example 19

Production of 2,5-dichlorobenzaldehyde

In a 50 ml three-necked flask equipped with a magnetic stirrer, a reflux condenser and a thermometer, 7.08 g (40 mmols) of 2,5-dichlorobenzyl alcohol and 10 ml of (166 mmols) of acetic acid were charged, followed by heating to 75° C. An aqueous solution prepared by dissolving 2.0 g (13.3 mmols) of sodium bromate in 8 ml of water was added dropwise over 2 hours, and then the mixture was stirred at 75° C. for 3 hours. An aqueous 5% sodium hydroxide solution was added to the system until the system is alkalified, followed by extraction with 200 ml of dichloromethane. The oil phase was washed in turn with water and saturated saline, and the solvent was distilled off under reduced pressure to obtain 6.8 g of an oil. The resulting oil was purified by silica gel column chromatography (ethyl acetate:n-hexane=1:4) to obtain 5.8 g of 2,5-dichlorobenzaldehyde. Yield: 82.9.

Example 20

Production of 4,4'-bisformylbiphenyl

In a 50 ml three-necked flask equipped with a magnetic stirrer, a reflux condenser and a thermometer, 4.28 g (20 mmols) of 4,4'-bishydroxymethylbiphenyl and 10 ml of (166 mmols) of acetic acid were charged, followed by heating to 75° C. An aqueous solution prepared by dissolving 2.04 g (13.5 mmols) of sodium bromate in 10 ml of water was added dropwise, and then the mixture was stirred at 75° C. until a color of bromine disappears. To the system, 50 ml of water was added and, after filtration, the resulting substance was dried to obtain 4.25 g of 4,4'-bisformylbiphenyl as a white crystal. Yield: 99.9%. It was confirmed by GS-MS that a molecular ion peak is 209.

INDUSTRIAL APPLICABILITY

As described above, according to the present invention, a novel method for industrial production of an aromatic aldehyde compound is provided.

According to the process of the present invention, an easily available benzyl compound (raw material benzyl compound) represented by a general formula (1) can be used as a raw material and the intended aromatic aldehyde compound can be produced by a simple operation in high selectivity without using an expensive catalyst or transition metal. Furthermore, since a harmful waste derived from the catalyst or transition metal is not produced in the process according to the present invention, a waste treatment can be easily conducted, and thus the process according to the present invention is environmentally friendly and is industrially useful.

The invention claimed is:

1. A process for producing an aromatic aldehyde compound represented by a general formula (3):

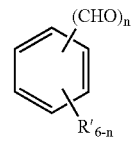

(3)

(wherein R' and n are as defined below), comprising: reacting a benzyl compound represented by a general formula (1):

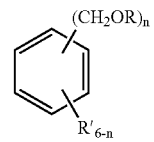

(1)

(wherein R represents a hydrogen atom or an alkyl group, n represents an integer of 1 to 6, and R' may be the same or different and each independently represents a hydrogen atom, an alkyl group, a hydroxyl group, an alkoxy group, a hydroxyalkyl group, an alkoxyalkyl group, a haloalkyl group, a carboxyl group or a metal salt thereof, an alkoxycarbonyl group, a halogen atom, a nitro group, an amino group, an alkylamino group, an alkylcarbonylamino group, a cyano group, a formyl group, an alkylcarbonyl group, or a phenyl group which may have a substituent), with an oxy-compound of bromine represented by a general formula (2):

 (2)

(wherein M represents a hydrogen atom or a metal atom, and m represents an integer of 1 to 3) in the presence of an acid catalyst selected from the group consisting of carboxylic acids, organic acids, Lewis acids, sulfuric acid, and phosphoric acid.

2. A process for producing an aromatic aldehyde compound according to claim 1, wherein, in the benzyl compound represented by a general formula (1), all R'(s) are hydrogen atoms or at least one of R'(s) is an electron-withdrawing group.

3. A process for producing an aromatic aldehyde compound according to claim 1, wherein, in the benzyl compound represented by a general formula (1), all R'(s) are hydrogen atoms or at least one of R'(s) is at least one of a nitro group, a chloro group and a hydroxymethyl group.

4. A process for producing an aromatic aldehyde compound according to any one of claims 1 to 3, wherein the oxy-compound of bromine represented by a general formula (2) is bromic acid, bromate or bromite.

5. A process for producing an aromatic aldehyde compound according to any one of claims 1 to 3, wherein the acid catalyst is an organic carboxylic acid.

* * * * *